United States Patent
Ilarionov et al.

(10) Patent No.: US 9,147,101 B2
(45) Date of Patent: Sep. 29, 2015

(54) METHOD OF DETECTING AND IDENTIFYING SUBSTANCES OR MIXTURES AND DETERMINING THEIR CHARACTERISTICS

(75) Inventors: Raycho Ilarionov, Gabrovo (BG); Ivan Simeonov, Gabrovo (BG); Nikolay Shopov, Plovdiv (BG)

(73) Assignee: Technical University Of Gabrovo, Gabrovo (BG)

( * ) Notice: Subject to any disclaimer, the term of this patent is extended or adjusted under 35 U.S.C. 154(b) by 107 days.

(21) Appl. No.: 13/985,325

(22) PCT Filed: Feb. 24, 2012

(86) PCT No.: PCT/BG2012/000005
§ 371 (c)(1),
(2), (4) Date: Aug. 22, 2013

(87) PCT Pub. No.: WO2012/113041
PCT Pub. Date: Aug. 30, 2012

(65) Prior Publication Data
US 2013/0322744 A1 Dec. 5, 2013

(30) Foreign Application Priority Data

Feb. 25, 2011 (BG) ........................ 110873

(51) Int. Cl.
*G06K 9/00* (2006.01)
*G01N 22/00* (2006.01)
*G06K 9/62* (2006.01)

(52) U.S. Cl.
CPC ............ *G06K 9/00087* (2013.01); *G01N 22/00* (2013.01); *G06K 9/6256* (2013.01)

(58) Field of Classification Search
CPC .. G01N 22/00; G06K 9/00087; G06K 9/6256
USPC .......................................... 382/159
See application file for complete search history.

(56) References Cited

U.S. PATENT DOCUMENTS

| 5,815,198 A * | 9/1998 | Vachtsevanos et al. ......... 348/88 |
| 7,409,374 B1 * | 8/2008 | Hohil et al. ..................... 706/20 |
| 2007/0105184 A1 * | 5/2007 | Greenbaum et al. ............. 435/29 |
| 2009/0167322 A1 * | 7/2009 | Magnuson et al. ........... 324/642 |
| 2010/0148071 A1 * | 6/2010 | Shioda ........................ 250/341.8 |
| 2011/0116605 A1 * | 5/2011 | Radley .......................... 378/162 |
| 2013/0322744 A1 * | 12/2013 | Ilarionov et al. .............. 382/159 |

* cited by examiner

*Primary Examiner* — Gregory M Desire
(74) *Attorney, Agent, or Firm* — Porter, Wright, Morris & Arthur, LLP

(57) ABSTRACT

This invention relates to a method of non-contact detection and identification of the type of different substances and mixtures as well as determining their characteristics as concentration, hardness, etc. The method comprises irradiation of the inspected object by a wave pulse or a series of such pulses; reception (1), amplification (2) and analog-to-digital conversion (3) of the signal, formation of output detailing wavelet coefficients and output approximating wavelet coefficients by means of fast discrete wavelet transformation of the digitized signal, by means of Mallat's pyramidal algorithm and orthogonal base functions, filtering (7) of the output approximating and detailing wavelet coefficients up to preselected ones, comparison of the filtered approximating and/or detailing wavelet coefficients, in the capacity of recognition attributes with preselected respective reference coefficients by the classifying device (8), and according to the comparison result the presence and type is determined and/or the studied characteristics of the inspected object is determined.

9 Claims, 1 Drawing Sheet

METHOD OF DETECTING AND IDENTIFYING SUBSTANCES OR MIXTURES AND DETERMINING THEIR CHARACTERISTICS

FIELD OF TECHNOLOGY

This invention relates to a method of non-contact detection and identification the type of different substances and mixtures as well as of determining their characteristics: concentration, hardness, etc.

This method can be employed in military industry, in security equipment, in research and in other fields of life for detecting explosives, recognition of materials, determining their hardness or concentration, detecting inadmissible ingredients in foods and articles, separating wastes for their recycling, etc.

DESCRIPTION OF PRIOR ART

A method of detection and identification of explosives is known by which the inspected object is irradiated by pulse ultra high-frequency (UHF) signals with specified values of the carrier frequency of the sounding impulses, of their durations and amplitudes, reception of the signal reflected by the controllable object, amplification and analogue-to-digital conversion of the received signal, measuring the parameter values of the converted signal and comparison with the prerecorded reference values of phase shifts corresponding to the dielectric properties of certain types of explosives. The controlled object is irradiated within frequency range of 300 MHz to 150 GHz, and the sounding impulse duration does not exceed 10 ms, the phase shift magnitude of the received signal is measured towards the emitted one and its intensity and by this magnitude the absorption factor of the controlled object is determined, the measured magnitude of phase shift of the received signal is compared to the emitted signal with reference values, where after, according to the comparison results and taking into account the determined absorption factor of the controlled object, the presence of explosive and its type is determined.

By the known method it is not possible to detect and identify other substances except explosives. Some technical impediments exist related to producing and using UHF signals, comparatively closer distance to the studied object is required, for one and the same power of irradiation of the controlled object. On the other hand, UHF signals have a harmful effect on human health.

TECHNICAL DESCRIPTION OF THE INVENTION

The object of this invention is to develop a method of non-contact detection and identification of substances or mixtures and/or of determining the characteristics of substances or mixtures which is fast and accurate enough at relatively lower frequency of the waves employed for irradiation of the inspected objects as well as to ensure enough safe distance to them when it is necessary.

A supplementary purpose of this invention is to reduce the prime cost and overall dimensions of equipment for non-contact control of this sort.

The objects have been solved by the proposed method which comprises:

1. Irradiation of the inspected object by a single wave pulse with a frequency of 20 kHz to 200 MHz and fixed duration or a sequence of such pulses;

2. Reception of the signal reflected by the inspected object by at least one receiver;

3. Amplification and analogue-to-digital conversion of the received signal up to at least 128 discrete values;

4. Formation of output detailing wavelet coefficients $D_{i,k}$ (where i varies from 1 to N) and of output approximating wavelet coefficients $A_N,k$ by means of fast discrete wavelet transformation of the digitized signal carried out by Mallat's pyramidal algorithm and orthogonal base functions (of Haar, of Daubechies, coiflets, simlets, etc.) when using a suitable number of transformation levels N, including high-frequency and low-frequency wavelet filtering and binary decimation after each filtering at each level i, until obtaining at least one approximating and at least one detailing wavelet coefficient after the last level of transformation whereat only the approximating wavelet coefficients $A_{i,k}$ are subjected to serial transformations by a wavelet filter at high frequencies and by a wavelet filter at low frequencies and binary decimation until the last level N is reached;

5. Filtering the output approximating $A_N,k$ and detailing $D_{i,k}$ wavelet coefficients up to preselected ones, according to the type of inspected object;

6. Comparison of the filtered approximating and/or detailing wavelet coefficients in their capacity of recognition attributes, with preselected respective reference coefficients by the classifying device, by a preselected method of image recognition (e.g.: "k nearest neighbours", neuron network, comparison to reference and other known methods), after that according to the comparison result the presence and type are determined and/or the examined characteristic of the inspected object is determined;

7. Output of resultant output signal which may serve for subsequent visualization, signaling or process control.

As a variant of the embodiment of the method, there is an option of manual or automatic shift of reference coefficients of the classifying device and respective shift of the filtering mask (shift in level and/or serial number k of the preselected output wavelet coefficients), according to the type of controlled object and manual or automatic shift in the image recognition method by means of a control device whereat the output approximating $A_{i,k}$ and detailing $D_{i,k}$ coefficients are stored in a buffer before being filtered, and the resultant output signal is output by the control device.

Another embodiment of the invention comprises training and/or self-training of the control device by input and accumulation of information in it about the output and filtered approximating and detailing coefficients and output information by the classifying device.

The advantages of this invention are as follows:
- The method is not applicable only to explosives and it has multi-purpose application;
- It has high speed and accuracy;
- It ensures enough distance from the emitters and receiver to the inspected object;
- The employed waves have frequency which does not have a harmful effect on human health or on the inspected object;
- The method ensures relatively low prime cost and low overall dimensions of the equipment operating by this method.

DESCRIPTION OF THE ATTACHED FIGURES

EMBODIMENTS OF THE INVENTION

The embodiments of the invention described below have been developed without restricting it only to the presented embodiments.

Embodiment 1

Figure 1:
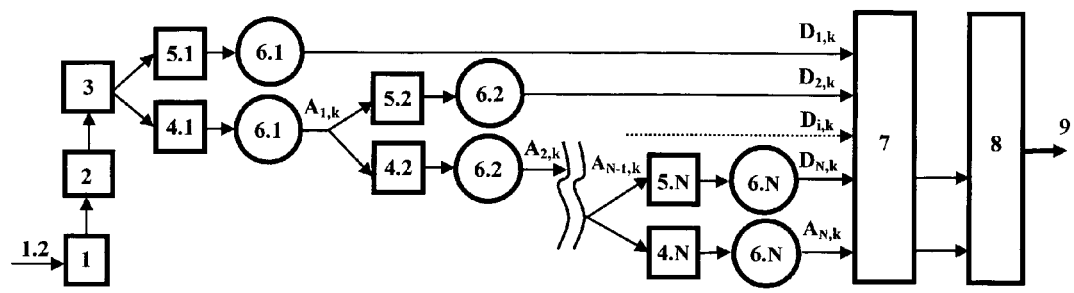
FIG. 1 is a block diagram of a method of detection and identification of substances or mixtures, and/or determining their characteristics by wavelet formation of recognition attributes.
Figure 3:
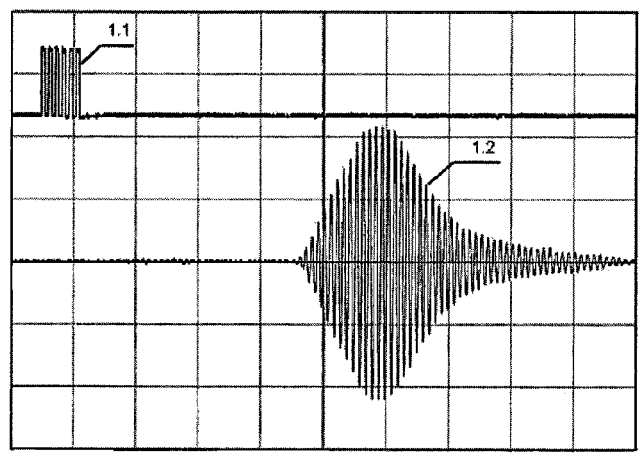
FIG. 3 shows a diagram of the pulse which excites the emitter and of the reflected wave pulse.

Referring to FIG. 1 a method of non-contact detection and identification of explosives has been invented which comprises:
  irradiation of the inspected object by a single wave pulse with frequency of 40 kHz, produced by a piezo-ceramic ultrasonic emitter (it is not shown) excited by a packet of six rectangular electrical pulses 1.1 with total duration of 150 μs (FIG. 3);
  reception of the signal reflected by the inspected object 1.2 by a piezo-ceramic ultrasonic receiver 1;
  amplification 2 and analogue-to-digital conversion 3 of the received signal up to 2500 discrete values, and the analogue-to-digital converter is activated at a preset time, depending on the distance to the inspected object.
  formation of output detailing wavelet coefficients Di,k and of output approximating wavelet coefficients $A_7$,k by means of fast wavelet transformation of the digitized signal, carried out by Mallat's pyramidal algorithm and Haar's and Simlet's base functions 5, when 7 levels of transformation N have been employed, comprising high-frequency 4.$i$ and low-frequency 5.$i$ wavelet filtering and binary decimation 6.$i$ (where i varies from 1 to N) after each filtering at each level i, whereat 20, respectively 28 approximating coefficients of the last level of transformation are obtained, but only the approximating wavelet coefficients Ai,k undergo serial transformations by a wavelet filter at high frequencies 4.$i$ and by a wavelet filter at low frequencies 5.$i$ and binary decimation 6.$i$ until the last $7^{th}$ level is reached;
  filtering the output approximating $A_7$,k and detailing Di,k wavelet coefficients up to preselected ones, but in this case only the output approximating coefficients $A_7$,k from the last level are transmitted, where k is 5, 10, 13, 16, 17, 18 and 20th (serial number of coefficient), in Haar's function, and k is 7, 10, 11, 13, 14, 16, 24, 25, 26 and 27th in Simlet's function 5;
  comparison of the filtered approximating wavelet coefficients $A_7$,k, in their capacity of recognition attributes with preselected respective reference coefficients by the classifying device 8, by a preselected method of image recognition—"k nearest neighbours", where after, according to the comparison result, the presence and type of explosive is determined;
  output of resultant output signal 9 which can serve for subsequent visualization, signaling or process control.

The classifying device 8 (FIG. 1) is preliminary synthesized by means of a training sample obtained on the basis of experiments conducted on identical objects (explosives Ammonal ZH-B-E, Ammonal E and trotyl) and formation of respective reference coefficients which are a subset of selected approximating coefficients from the set of all output approximating and detailing coefficients obtained from the training sample and the selection is performed by a criterion of general error minimum and by means of consecutive rejection method (a method of attribute selection from the image recognition theory).

A total of 870 measurements have been taken and the training sample (450 measurements) has been formed by a random choice of the numbers of measurements. A check sample (420 measurements) has also been formed consisting of the measurements which are not included in the training sample. The distribution of explosive types is equal for each sample.

The results of reference coefficient selection and errors of the method concerning the check sample are given in Table 1.

TABLE 1

| Transformation level | Base function used | Selected approximating coefficients (attributes) | Selected detailing coefficients (attributes) | Type of inspected object | Actual error, % | Major error, % | General error, % |
|---|---|---|---|---|---|---|---|
| 7 | Haar (Daubechies 1) | A7, k, where: k = 5, 10, 13, 16, 17, 18 и 20 | none | 1. Ammonal - ZH-B-E | 0.00 | 0.00 | 0.95 |
|  |  |  |  | 2. Ammonal E | 0.00 | 2.85 |  |
|  |  |  |  | 3. Trotyl | 2.78 | 0.00 |  |
| 7 | Simlet 5 | A7, k, where: k = 7, 10, 11, 13, 14, 16, 24, 25, 26 и 27 | none | 1. Ammonal - ZH-B-E | 6.57 | 8.57 | 6.19 |
|  |  |  |  | 2. Ammonal E | 4.44 | 7.86 |  |
|  |  |  |  | 3. Trotyl | 7.43 | 2.14 |  |

Embodiment 2

Referring to FIG. 1, a method of detecting and identifying metals and/or their alloys has been invented.

The method comprises the actions described in Embodiment 1 and the inspected object is also irradiated by a single wave pulse with frequency of 40 kHz, produced by piezo-ceramic ultrasonic emitter excited in a manner similar to Embodiment 1 (FIG. 3), followed by reception 1, amplification 2 and analogue-to-digital conversion 3 of the received signal up to 2500 discrete values and the analogue-to-digital converter is activated at a preset level.

Figure 2:
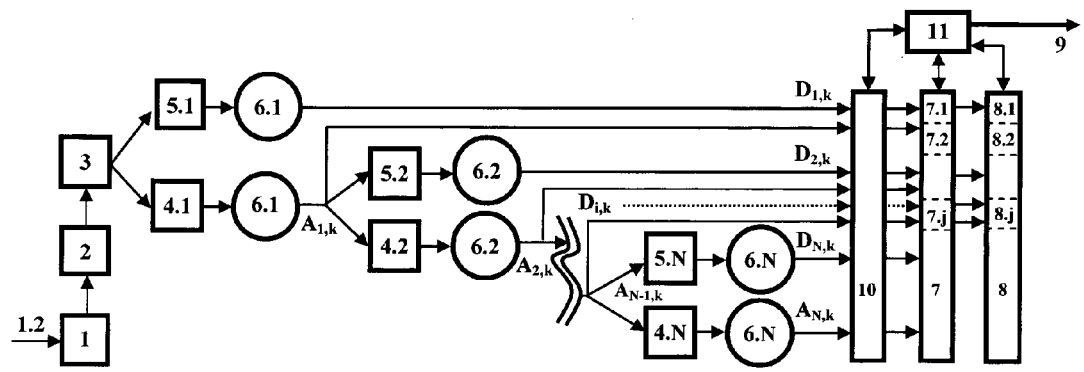
FIG. 2 is a block diagram of the method according to the invention with buffering the output wavelet coefficients and control device.

The digitized signal is processed by means of fast discrete wavelet transformation performed by Mallat's pyramidal algorithm and Haar's orthogonal base functions with the employment of 8 transformation levels comprising high-frequency 4.$i$ and low-frequency 5.$i$ wavelet filtering and binary decimation 6.$i$ after each filtering at each level whereupon output detailing Di,k and approximating $A_8$,k coefficients are formed (FIG. 1 and FIG. 2).

The output approximating and detailing coefficients are filtered up to preselected ones and in this case only the output approximating coefficient $A_8$,k is transmitted, where k is the $4^{th}$ serial coefficient in Haar's function.

The filtered approximating coefficient $A_8,k$, in the capacity of recognition attribute is compared to a preselected reference coefficient by the classifying device 8, by a preselected image recognition method: 'reference comparison' where after, according to the comparison results, the presence and type of metal or alloy is determined and a resultant output signal 9 is output which can serve for subsequent visualization, signaling or process control.

The classifying device 8 has been synthesized preliminary by means of a training sample obtained on the basis of experiments conducted on identical metals and alloys and formation of respective reference coefficients which are a subset of selected approximated coefficients from the set of all output approximating and detailing coefficients obtained from the training sample and the selection is made by the criterion of general error minimum and by the method of serial selection (a method of attribute selection from the image recognition theory).

Aluminium, chrome-nickel steel, brass, copper, structural steel and cast iron have been examined and a total of 420 measurements have been taken (70 measurements per object), from which a training sample (220 measurements) and check sample (200 measurements) have been formed at random and the latter consists of measurements which are not included in the training sample.

The results of selecting reference coefficients and errors of the method concerning the check sample are shown in Table 2.

frequency $5.i$ wavelet filtering and binary decimation $6.i$ after each filtering at each level, where upon the output detailing Di,k and approximating $A_8$,k coefficients are formed (FIG. 1 and FIG. 2);

The output approximating and detailing coefficients are filtered up to preselected ones and in this case only the output approximating coefficient $A_8$,k is transmitted, where k is the $7^{th}$ serial coefficient in Haar's function;

The filtered approximating coefficient $A_8$,k, in its capacity of recognition attribute is compared to a preselected respective reference coefficient by the classifying device 8, by a preselected method of image recognition: 'k nearest neighbours' where after, according to the comparison result, the presence and type of plastics is determined.

Four of the most commonly used thermoplastic plastics have been tested: low density polyethylene (LDPE), polyethyleneterephthalate (PET), polystyrene (PS), polyvinylchloride (PVC), by taking 360 measurements. From the data obtained about the objects, training and check samples have been formed and the training sample has been formed by the method of self-random sampling with reselection. This sample is used for the synthesis of the classifying device 8 (FIG. 1 and FIG. 2), operating by the method of 'k nearest neighbours', and its operating capacity has been tested by means of an independent check sample of 240 measurements.

Table 3 summarizes the results of identifying the plastics in the check sample.

TABLE 2

| Level of transformation | Base function used | Selected approx. coefficients (attributes) | Selected detailing coefficients (attributes) | Type of inspected object | Actual error % | Major error % |
|---|---|---|---|---|---|---|
| 8 | Haar (Daubechies 1) | A8, k where: k = 4 | none | aluminium | 0 | 0 |
|  |  |  |  | chrome-nickel steel | 0 | 0 |
|  |  |  |  | brass | 0 | 0 |
|  |  |  |  | copper | 0 | 0 |
|  |  |  |  | structural steel | 0 | 0 |
|  |  |  |  | cast iron | 0 | 0 |
|  |  | General error: |  |  |  | 0% |

Embodiment 3

A method has been created according to the present invention which has been applied to the detection and identification of plastics (FIG. 1).

The method comprises the actions described above in Embodiments 1 and 2, and the irradiation of the inspected object is also by a single wave pulse with frequency of 40 kHz, produced by a piezo-ceramic ultrasonic emitter, followed by reception 1, amplification 2 and analogue-to-digital conversion 3 of the received signal up to 2500 discrete values and the analogue-to-digital converter is activated at a preset level.

The digitized signal is processed by means of fast discrete wavelet transformation by Mallat's pyramidal algorithm and Haar's orthogonal base functions, employing 8 levels of transformation which include high frequency $4.i$ and low

TABLE 3

| Type of inspected object | Identified by the classifying device for selected attributes: A8, k, where: k = 7 | | | | Total number | Errors | |
|---|---|---|---|---|---|---|---|
|  | LDPE | PET | PS1 | PVC |  | Actual, % | Major, % |
| LDPE | 77 | 0 | 0 | 0 | 77 | 0 | 0 |
| PET | 0 | 53 | 0 | 0 | 53 | 0 | 0 |
| PS1 | 0 | 0 | 54 | 0 | 54 | 0 | 0 |
| PVC | 0 | 0 | 0 | 56 | 56 | 0 | 0 |
| Total | 77 | 53 | 54 | 56 | 240 | General error - 0% | |

Embodiment 4

A method has been invented of determining the concentration of alcohol solutions, in particular, ethanol.

The method differs from Embodiments 1, 2 and 3 by the following features:
- frequency of the single wave pulse—125 kHz;
- number of discrete values after analogue-to-digital conversion—2 500;
- orthogonal base function used for fast discrete wavelet transformation—Haar;
- levels of fast discrete wavelet transformation—8;
- preselected recognition attributes—only approximating wavelet coefficients—$A_8,k$, where k is 4, 5, 7, 8 and 10 (serial number of coefficient);
- method of comparison of the classifying device—"k nearest neighbours".

The classifying device 8 (FIG. 1 and FIG. 2) has been preliminary synthesized by means of a training sample obtained on the basis of conducted experiments. Pure water-alcoholic solutions with ethanol content of 20%, 40%, 60% and 80% have been studied and a total of 498 measurements have been taken.

The training sample includes 250 measurements and it is formed by the method of self-random samples with reselection by means of random selection.

The operating capacity of the classifying device 8 has been tested by means of an independent check sample (248 measurements), which includes all measurements out of the training sample. The results are shown in Table 4.

TABLE 4

| Type of inspected object | Determined by the classifying device For selected attributes: A8, k, where: k = 4, 5, 7, 8, and 10 | | | | | Errors | |
|---|---|---|---|---|---|---|---|
| | 20% ethanol | 40% ethanol | 60% ethanol | 80% ethanol | Total number | Actual, % | Major, % |
| 20% ethanol | 58 | 2 | 0 | 0 | 60 | 3.33 | 3.33 |
| 40% ethanol | 2 | 58 | 2 | 0 | 62 | 4.92 | 6.45 |
| 60% ethanol | 0 | 1 | 61 | 2 | 64 | 7.58 | 4.69 |
| 80% ethanol | 0 | 0 | 3 | 59 | 62 | 3.28 | 4.84 |
| total | 60 | 61 | 66 | 61 | 248 | General error - 4.84% | |

Embodiment 5

A method of determining the fat content of milk has been developed.

The method differs from the embodiments described above by the following features:
- frequency of the single wave pulse—40 kHz;
- number of discrete values after analogue-to-digital conversion—6000;
- orthogonal base function used for fast discrete wavelet transformation—Haar;
- levels of fast discrete wavelet transformation—9;
- preselected recognition attributes—wavelet coefficients—$A_9,k$, where: k=2, 5, 7, 8, 9 and 12 and $D_9,k$, where: k=1, 2, 3, 5 (serial number of coefficient);
- method of comparison of the classifying device—"k nearest neighbours".

The classifying device 8 (FIG. 1 and FIG. 2) is preliminary synthesized by means of a training sample obtained on the basis of conducted experiments. Data are obtained when testing milk with different fat contents measured with a different apparatus—"Ekomilk" (manufactured by Bulteh 2000 Ltd, in the town of Stara Zagora).

The accuracy of the method has been evaluated after classifying the check sample containing 468 measurements. The results are summarized in Table 5.

TABLE 5

| Level of transformation | Base function used | Selected approximating coefficients (attributes) | Selected detailing coefficients (attributes) | Type of inspected object (fat content, %) | Actual error % | Major error % |
|---|---|---|---|---|---|---|
| 8 | Haar (Daubechies 1) | A9, k where: k = 2, 5, 7, 8, 9 and 12 | D9, k where: k = 1, 2, 3 and 5 | below 0.40 | 5.71 | 8.33 |
| | | | | 0.7 | 8.33 | 8.33 |
| | | | | 1.0 | 8.11 | 5.56 |
| | | | | 1.2 | 2.86 | 5.56 |
| | | | | 1.6 | 5.41 | 2.78 |
| | | | | 1.8 | 2.78 | 2.78 |
| | | | | 2.0 | 5.71 | 8.33 |
| | | | | 2.2 | 5.56 | 5.56 |
| | | | | 2.4 | 5.41 | 2.78 |
| | | | | 2.7 | 5.56 | 5.56 |
| | | | | 2.9 | 8.33 | 8.33 |
| | | | | 3.1 | 5.41 | 2.78 |
| | | | | above 3.2 | 2.86 | 5.56 |
| | | | General error: | | 5.56% | |

Embodiment 6

A method of determining the fat content of yoghurt has been developed.

The method differs from the embodiments described above by the following features:
- frequency of the single wave pulse—40 kHz;
- number of discrete values after analogue-to-digital conversion—2500;
- orthogonal base function used for fast discrete wavelet transformation—Coiflet 1;
- levels of fast discrete wavelet transformation—8;
- preselected recognition attributes—wavelet coefficients—$A_8,k$, where: k=7, 8, 9 and $D_8,k$, where: k=3, 4, 6, 7, 8 (serial number of coefficient);
- method of comparison of the classifying device—"k nearest neighbours".

Classifying device 8 (FIG. 1 and FIG. 2) is synthesized by means of a training sample obtained on the basis of conducted experiments. Data are obtained by testing yoghurt with five different fat contents (written by the producer).

Training and check samples are formed from output data. The training sample is formed by the method of self-random samples with reselection, by random selection of the measurement numbers and it contains 300 measurements. The check sample has 435 measurements and it has been formed by selecting measurements which are not included in the training sample.

The classification attributes have been selected by the serial selection method.

The results relative to the check sample are given in Table 6.

TABLE 6

| Type of inspected object | Determined by the classifying device for selected attributes: $A_8, k$, where: k = 7, 8, 9 and $D_8, k$, where: k = 3, 4, 6, 7, 8 | | | | | Total | Errors | |
|---|---|---|---|---|---|---|---|---|
| | Fat content: | | | | | | Actual, | |
| (fat content) | 1% | 2% | 3% | 3.6% | 5% | number | % | Major, % |
| 1% | 54 | 1 | 0 | 0 | 0 | 55 | 5.26 | 1.82 |
| 2% | 2 | 150 | 3 | 0 | 0 | 155 | 4.46 | 3.23 |
| 3% | 0 | 4 | 78 | 3 | 0 | 85 | 8.24 | 8.24 |
| 3.6% | 1 | 2 | 4 | 77 | 1 | 85 | 6.10 | 9.41 |
| 5% | 0 | 0 | 0 | 2 | 53 | 55 | 1.85 | 3.64 |
| Total | 57 | 157 | 85 | 82 | 54 | 435 | General error - 5.29% | |

Embodiment 7

A method of determining the hardness of materials, in particular metals, has been developed.

The method differs from the embodiments described above by the following features:
- frequency of the single wave pulse—40 kHz;
- number of discrete values after analogue-to-digital conversion—3500;
- orthogonal base function used for fast discrete wavelet transformation—Simlet 1;
- levels of fast discrete wavelet transformation—9;
- preselected recognition attributes—none, all approximating and detailing wavelet coefficients are used;
- method of comparison of the classifying device—"artificial neuron network".

Classifying device 8 (FIG. 1 and FIG. 2) has been synthesized by means of building an artificial neuron network (ANN) and its training, based on conducted experiments.

To this end, 4 identical specimens of X40 steel and dimensions: Φ50 mm, thickness: 10 mm and Rockwell hardness: HRc=34, HRc=36, HRc=40, HRc=46 and HRc=50 have been made.

100 measurements per specimen have been taken, a total of 400 for specimens of the same hardness. Training and check samples have been formed from output data. The training sample has been formed by the method of self-random samples with reselection, by a random selection of measurement numbers and contains 300 measurements. The check sample contains 100 measurements and has been formed by means of selection of measurements which are not included in the training sample without reselection.

Approximating $A_9,k$ and detailing $D_9,k$ coefficients obtained from the training sample after wavelet transformation, in their capacity of recognition attributes, are supplied for training the neuron classifying device 8.

In order to find an optimum solution to accuracy and speed of results, the ANN structure has been developed so that it allows alterations.

In this individual case, the neuron network has been designed with 14 inputs, an intermediate layer and one output. The number of inputs is determined by the number of approximating $A_9,k$ and detailing $D_9,k$ coefficients.

At the ANN inputs the values of the approximating and detailing coefficients are supplied. At the output a number is obtained which indicates to which type the material being recognized belongs. The recognition range for a specimen is ±0.5 units of the nominal value of certain hardness. For instance, X40 steel with hardness HRc=46 is coded by 4. If at the output of the neuron network, a signal ranging within 3.5 to 4.5 is received, it is considered that the specimen has been recognized successfully and it is added to this class.

Training data are input for recognition into ANN 5 times each, and check data—10 times each. Table 7 shows the results obtained when recognizing the specimens.

TABLE 7

| Type No | Hardness HRc | Type of sample | Number of correct responses | Recognition error, % |
|---|---|---|---|---|
| 1 | 34 | training | 300/300 | 0 |
| | | check | 96/100 | 4 |
| 2 | 36 | training | 300/300 | 0 |
| | | check | 92/100 | 8 |
| 3 | 40 | training | 300/300 | 0 |
| | | check | 99/100 | 1 |
| 4 | 46 | training | 300/300 | 0 |
| | | check | 98/100 | 2 |
| 5 | 50 | training | 300/300 | 0 |
| | | check | 96/100 | 4 |

Embodiment 8

A method of detection and identification of substances and mixtures in groups has been developed (FIG. 2).

To this end, the sequence of operations described in Embodiments from 1 to 7 is performed and in this case an additional option is provided for manual or automatic shift of the reference coefficients of a multiple classifying device 8 and respective shift of the filtering masks 7*j* (shift in level N and serial number k of the preselected output coefficients), according to the types of inspected objects for which reference coefficients are available (i.e. for which the multiple classifying device 8 has been trained, for example, explosives, alcohols and hard metals), as well as manual or automatic shift of the image recognition method by means of control device 11, whereat output approximating Ai,k and detailing Di,k coefficients are stored in buffer 10 before they enter to be filtered 7, and the resultant output signal 9 is output by the control device after processing all intermediate resultant signals 9j.

According to the design of the control device, it is possible the device to be trained or self-trained by inputting and accumulating in it information about the output and filtered approximating and detailing coefficients and output information by the classifying device.

Embodiment 9

A method of determining various characteristics of one and the same inspected object (FIG. 2) has been developed, e.g., determining the fat content, dry substance and inadmissible ingredients in milk.

This method is analogous to Embodiment 8 and its specific feature is that a multiple classifying device 8 and buffer 10 are available again, the buffer however supplies in sequence for filtering 7 approximating and/or detailing coefficients which correspond to at least two of the studied characteristics (for which preselected reference coefficients are available) and this process is controlled manually or automatically by a control device 11.

Applications of the Invention

The applications of the method according to the invention have been shown in the described preferred embodiments but they do not restrict it only to the listed fields of usage. In practice, by the proposed method all sorts of substances or mixtures can be detected and identified and/or one or more characteristics of theirs can be determined as well and it is enough if a preliminary synthesized classifying device is available.

In order to achieve sufficient accuracy of the method, of essential importance is the suitable selection of wavelet function for transformation for each individual inspected object, the choice of transformation level, as well as the proper selection of reference approximating and/or detailing coefficients (recognition attributes) and also the degree of training of the classifying device.

To implement the method correctly and more accurately, it is required to study the results when using various orthogonal base wavelet functions at various transformation levels, different image recognition methods and methods of attribute selection and for different number of approximating and/or detailing coefficients used, until the error is minimized.

The reference approximating and/or detailing coefficients are selected on the basis of preliminary obtained data from measurements taken of known concrete objects (training sample) and by means of a method of consecutive rejection, serial selection method or another known method of selecting recognition attributes.

To train the classifying device correctly, the measurements which provide the data for the training should be taken of entirely and unambiguously defined objects whose characteristics have been measured by at least one more accurate method.

REFERENCES

1. Patent RU 2283485.

What is claimed is:

1. Method of detecting and identifying substances or mixtures and/or determining their characteristics, said method comprising the steps of:
    irradiating an inspected object by pulse signals of fixed duration,
    receiving a signal reflected by the inspected object;
    amplifying and analog-to-digital converting the received signal and comparison of parameters of the converted signal to prerecorded reference values; and
    wherein the inspected object is irradiated by a single wave pulse with a frequency of 20 kHz to 200 MHz or a series of such pulses, the analogue-to-digital conversion of the received signal is up to at least 128 discrete values and followed by the steps of:
        forming of output detailing wavelet coefficients Di,k (where i varies from 1 to N) and of output approximating wavelet coefficients AN,k by means of fast discrete wavelet transformation of the digitized signal, performed by Mallet's pyramidal algorithm and orthogonal base functions, when using a suitable number of transformation levels N, comprising high frequency (4.i) and low frequency (5.i) wavelet filtering and binary decimation (6.i) after each filtering at each level i, until at least one approximating and at least one detailing wavelet coefficient is obtained after the last transformation level, whereat only the approximating wavelet coefficients Ai,k are subjected to successive transformation by a wavelet filter at high frequencies (4.i) and by a wavelet filter at low frequencies (5.i) and binary decimation (6.i), until the last level N is reached;
        filtering (7) of the output approximating AN,k and detailing Di,k wavelet coefficients up to preselected ones, according to the type of inspected object; and
        comparing the filtered approximating and/or detailing wavelet coefficients in their capacity of recognition attributes with preselected respective reference coefficients by classifying device (8), by a preselected image recognition method, where after, according to the comparison result, the presence and type is determined and/or the studied characteristics of the inspected object is determined.

2. A method as claimed in claim 1, wherein the reference coefficients of the classifying device (8) are shifted manually of automatically and respectively the filtering mask is shifted according to the type of the inspected object, as well as the image recognition method is shifted manually or automatically by a control device (11), whereat the output approximating Ai,k and detailing Di,k coefficients are stored in a buffer (10) before being filtered (7).

3. A method as claimed in claim 2, wherein the control device (11) is trained and/or self trained by inputting and accumulating in it information about the output and filtered approximating and detailing coefficients and output information by the classifying device (8).

4. A method according to any one of claim 1, 2 or 3, wherein the classifying device (8) has been preliminary synthesized by means of a training sample obtained on the basis of conducted experiments on identical objects and formation of respective reference coefficients which are a subset of selected approximating and/or detailing coefficients of the set of all output approximating and detailing coefficients obtained from the training sample and the selection is made by the criterion of general error minimum and by means of a known method of attribute selection from the image recognition theory.

5. A method according to claim 4 wherein after the comparison, a resultant output signal (9) is output by the classifying device (8) or by the control device (11), and this signal serves for subsequent visualization, signaling or process control.

6. A method according to claim 4 wherein during the analog-to-digital conversion (3) of the received signal, the activation of the analog-to-digital converter is at preset time, depending on the distance to the inspected object or it is at preset level of the signal.

7. A method according to any one of claim 1, 2 or 3 wherein after the comparison, a resultant output signal (9) is output by the classifying device (8) or by the control device (11), and this signal serves for subsequent visualization, signaling or process control.

8. A method according to claim 7 wherein during the analog-to-digital conversion (3) of the received signal, the activation of the analog-to-digital converter is at preset time, depending on the distance to the inspected object or it is at preset level of the signal.

9. A method according to any one of claim 1, 2 or 3 wherein during the analogue-to-digital conversion (3) of the received signal, the activation of the analogue-to-digital converter is at preset time, depending on the distance to the inspected object or it is at preset level of the signal.

* * * * *